US009290434B2

(12) United States Patent
Verhaeghe et al.

(10) Patent No.: US 9,290,434 B2
(45) Date of Patent: Mar. 22, 2016

(54) LUBRICITY IMPROVER

(75) Inventors: Ben Verhaeghe, Rijkevorsel (BE);
Lieven Van Hecke, Antwerpen (BE);
Dirk Packet, Leuven (BE)

(73) Assignee: OLEON, Ertvelde (BE)

( * ) Notice: Subject to any disclaimer, the term of this patent is extended or adjusted under 35 U.S.C. 154(b) by 167 days.

(21) Appl. No.: 14/116,019

(22) PCT Filed: May 6, 2011

(86) PCT No.: PCT/EP2011/057362
§ 371 (c)(1),
(2), (4) Date: Feb. 18, 2014

(87) PCT Pub. No.: WO2012/152309
PCT Pub. Date: Nov. 15, 2012

(65) Prior Publication Data
US 2014/0162922 A1 Jun. 12, 2014

(51) Int. Cl.
*C07C 69/33* (2006.01)
*C10L 1/19* (2006.01)
*C10L 10/08* (2006.01)
*C10M 129/76* (2006.01)
*C07C 57/03* (2006.01)
*C07C 69/734* (2006.01)

(52) U.S. Cl.
CPC ............... *C07C 69/33* (2013.01); *C10L 1/191* (2013.01); *C10L 10/08* (2013.01); *C10M 129/76* (2013.01); *C07C 57/03* (2013.01); *C07C 69/734* (2013.01); *C10L 2200/0446* (2013.01)

(58) Field of Classification Search
CPC ...... C07C 57/03; C07C 69/33; C07C 69/734; C07C 59/42; C07C 3/003; C10M 129/76; C10M 129/78
See application file for complete search history.

(56) References Cited

U.S. PATENT DOCUMENTS

| 2,672,444 | A |   | 3/1954 | Wasson |
| 3,968,169 | A |   | 7/1976 | Seiden et al. |
| 4,214,038 | A | * | 7/1980 | McCarty ............... C11D 1/667 222/635 |
| 4,957,651 | A | * | 9/1990 | Schwind ....................... 508/331 |
| 5,632,785 | A | * | 5/1997 | Culotta ........................... 44/389 |

FOREIGN PATENT DOCUMENTS

| DE | 19614722 A1 | 10/1997 | |
| DE | 19949518 | * 4/2001 | ............. C07C 69/52 |
| DE | 19949518 A1 | 4/2001 | |

(Continued)

OTHER PUBLICATIONS

WO2006053664, Dierker, M. et al., Additive of improving the lubricating properties of diesel oils, 2006, English translation, 6 pages.*

(Continued)

*Primary Examiner* — Yate K Cutliff
(74) *Attorney, Agent, or Firm* — Scully Scott Murphy and Presser

(57) ABSTRACT

The present invention relates to the use of a composition comprising a partial ester of a carboxylic acid and a polyhydric alcohol as a lubricity improver, wherein as the polyhydric alcohol use is made of a diglycerol composition which comprises at least 75.0 wt. % of diglycerol, wherein as the carboxylic acid use is made of a fatty acid composition which contains at least one C8-C22 fatty acid or a mixture of two or more thereof.

22 Claims, 4 Drawing Sheets

(56) References Cited

FOREIGN PATENT DOCUMENTS

| | | | | |
|---|---|---|---|---|
| EP | 0612833 A1 | | 8/1994 | |
| EP | 0826765 A1 | | 3/1998 | |
| FR | 781842 | * | 5/1935 | ............. C07C 69/33 |
| GB | 775089 | | 5/1957 | |
| GB | 1033658 | | 6/1966 | |
| WO | WO 01/19941 A1 | | 3/2001 | |
| WO | WO2006053664 | * | 5/2006 | ................ C10L 1/19 |
| WO | WO 2006053664 A1 | | 5/2006 | |

OTHER PUBLICATIONS

DE19949518, Lagarden, M. et al., Novel primary mono-fatty acid esters of glycerol self-condensation products, useful as surfactants in cosmetics, pharmaceuticals, foods, detergents or cleaning compositons, comprises specific structure, 2001, English translation 36 pages.*

FR781842, Emusol Corp, Hydrophilic fats and their manufacturng processes, 1935, English translation 10 pages.*

Garcia, E. et al., Optimization of the Enzymatic Esterification of Diglycerol and Lauric Acid, Journal of Surfactants and Detergents, (2001), vol. 4, No. 3, pp. 257-262.

Wei, D. et al., The Lubricity of Diesel Fuels, Wear, (1986), vol. 111, pp. 217-235.

International Search Report and Written Opinion dated Feb. 6, 2012 issued in PCT/EP2011/057362.

* cited by examiner

LUBRICITY IMPROVER

BACKGROUND OF THE DISCLOSURE

The present invention relates to the use of a composition comprising a partial ester of a carboxylic acid and a polyhydric alcohol as a lubricity improver.

Over the years, commercially available fuel systems have become more and more refined. Processes have been developed to reduce sulphur levels and levels of aromatics, in particular for diesel fuel, where it has been proposed to limit the maximum distillation point of diesel fuel. However, with these pre-treatment processes lubricating properties provided by the fuel itself became worse. In relation to low density and low viscosity fuel systems such as naphta, kerosene and gas condensates, it has been observed that they show poor lubricity to metal surfaces. As a result of these poor lubrification properties, critical components such as fuel pumps and gas turbine flow dividers risk to show serious and accelerated wear upon use, which may result in premature failure. Therefore, increasing attention has been given to the addition of lubricity improving additives to fuel, with the purpose of imparting acceptable lubricating properties back to the fuel.

To balance the needs of engine makers and users, standards officials and fuels producers, the ASTM D-6079 diesel lubricity specification has been put forward, which states that a standardized wear test should not create a "wear scar" larger that 520 microns in diameter. The test makes use of a High Frequency Reciprocating Rig (HFRR) as described in D. Wei and H. Spikes, Wear, Vol. 111, N) 2, p. 217, 1986 and R. Caprotti et al, SAE paper 922183; SAE fuels and lubes, Meeting October 1992, San Fransisco USA. Although various injector and injector pump tests and several laboratory tests have been developed to measure the lubricity of diesel fuels, ASTM D6079 High Frequency Reciprocating Rig ("HFRR") test is the most widely used and accepted.

The use of esters of long chain fatty acids as fuel lubricity additives is well known in the art, and a wide variety of additive compositions are commercially available, with the additive being optimised in function of the fuel with which it is to be used. Properties that are considered to be of importance with lubricity improvers include the following: the concentration of metal contaminants should be as small as possible, the lubricity improver should show excellent mixing ability and compatibility with the envisaged type of fuel and a minimal tendency to form gum deposits, the lubricity improver should have a low solids content and the risk to the occurrence of adverse interactions with traces of iron and other fuel additives present in the fuel, such as corrosion inhibitors, combustion improvers etc, should be negligible.

EP1216288 discloses the use of a diester of a monocarboxylic acid and a polyhydric alcohol as a lubricity improver for diesel fuel oil. The product is said to show an improved cold stability, in particular a reduced tendency to cloud or freeze at temperatures below 10° C. The monocarboxylic acid comprises a $C_8$-$C_{24}$ linear or branched chain unsaturated fatty acid or a mixture thereof, preferably a $C_{12}$-$C_{22}$ unsaturated fatty acid. The carboxylic acid typically has an iodine value of 40 to 180 in accordance with the AOCS Method cd-1-25. Oleic acid, linoleic acid, linolenic acid, palmitoleic acid, gadoleic acid, erucic acid and other unsaturated acids with 22 carbon atoms are particularly preferred. The unsaturated carboxylic acid component may be selected from tall oil fatty acids, soybean fatty acids, rape seed fatty acids, sunflower seed fatty acids, fish oil and cold fractionated tallow and palm oil fatty acids. The polyhydric alcohol comprises an alcohol of the general formula $$CR^1R^2R^3R^4 \qquad \text{(formula 1)}$$

or a dimer, a trimer or tetramer of the alcohol obtainable by condensation of the alcohol of formula 1. In formula 1, $R^1$, $R^2$, $R^3$ are each independently of each other a $C_1$-$C_{12}$ linear or branched chain alkylol and $R^4$ is a linear or branched chain $C_1$-$C_{12}$ alkyl or a linear or branched chain $C_1$-$C_{12}$ alkylol. The diester may be part of a mixture including higher esters such as triesters and tetraesters. It is explained that the diesters have a cold stability which is independent of the molar ratio of the fatty acid to alcohol. Lubricity efficiency is said to increase with a decreasing ratio of fatty acid to alcohol for both mono- and di-esters, whereas with monoesters the cold stability seems to decrease.

The lubricity improving compositions disclosed in EP826765 have been developed for the purpose of improving the lubricating capacity of "average petroleum distillates" for use with engines, gas turbines or diesel engines. The lubricity improvers disclosed in EP826765 include partial esters of at least one polyol and at least one monocarboxylic acid. Suitable polyols include propanediol-1,2, propanediol-1,3, the butanediol-1,3, butanediol-1,4, neopentyl-glycol, glycerol, diglycerol, polyglycerols, trimethylolpropane and pentaerythritol and mixtures containing two or more thereof. Suitable monocarboxylic acids include those having between 4 and 24 carbon atoms, for example butyric, caproic, caprylic, capric, lauric, myristic, palmitic, palmitoleic, stearic, oleic, linoleic, ricinoleic, arachidic, gadoleic, behenic, erucic and lignoceric acid. Particularly preferred are di-esters of glycerol or di-esters of glycerol in a mixture with mono esters. The examples disclose mixtures of 37% respectively 55% of monoglycerides and 62% respectively 45% of diglycerides.

DE19614722 discloses lubricity improvers with an improved cold stability, which mainly consist of mixtures of mono- and diesters of unsaturated fatty acids with 16-22 carbon atoms and at least two different polyols with 3-10 carbon atoms and 3-6 hydroxyl groups. Preferred polyols are trimethylolpropane, pentaerythritol and dipentaerythritol in a molar of 1:3 to 3:1. Suitable fatty acids include oleic acid, linoleic acid, linolenic acid.

To date, attempts to improve lubrication properties of esters of fatty acids and polyols, mainly concentrated on optimising the fatty acid composition. Applications of diglycerol esters remained limited until today, and were mostly situated in the field of cosmetics.

The present invention seeks to further improve lubricating properties provided by fatty acid ester compositions.

DETAILED DESCRIPTION

The present invention therefore relates to the use of fatty ester compositions as a lubricity improver, in particular to the use of fatty ester compositions with the purpose of further improving lubricating properties of fuel oil and engine oil.

This is achieved according to the invention with the technical features of the characterising portion of the first claim.

Thereto, the lubricity improver of the present invention is characterised in that as the polyhydric alcohol use is made of a diglycerol composition which comprises at least 75.0 wt. % of diglycerol and in that the as the fatty acid use is made of at least one $C_8$-$C_{22}$ fatty acid or a mixture of two or more thereof.

The at least one $C_8$-$C_{22}$ fatty acid or a mixture of two or more thereof may contain linear or branched chain, which may be saturated or contain one or more unsaturated bonds, which may be substituted or not. Usually the fatty acid will be commercially available as a mixture of several fatty acids.

The inventors have observed that diglycerol is commercially available as a mixture of several compounds, which contains diglycerol and other polyols. The chemical composition of commercially available diglycerol compositions may vary substantially depending a.o. on its production process. Commercially available diglycerol compositions have been found to include besides diglycerol, monoglycerol which may be present in a concentration up to 40 wt. %, triglycerol, tetraglycerol and pentaglycerol which together may be present in concentrations up to 25 wt. % or more. The inventors have now found that by using a diglycerol composition with (i) an enhanced content of diglycerol of at least 75.0 wt. %, and (ii) a reduced content of glycerol and other polyols conventionally present in commercially available diglycerol compositions, diglycerol fatty acid esters may be obtained with improved lubricating properties. By adding the diglycerol fatty acid esters of the present invention to a fuel composition, in particular a fuel oil composition, or to a lubricating composition, a lubricating film may be build which shows good affinity in particular for metal surfaces and good cohesion. Use of the fatty acid diglycerol ester of this invention in lubricating and fuel compositions permits improving their lubrication properties and further reducing friction between moving parts and wearing when compared to conventional diglycerol esters and esters of higher polyols. It is believed that the better the purity of the diglycerol composition and the smaller the concentration of polyols other than diglycerol, the higher the affinity in particular for metal surfaces and the better film forming properties may be achieved.

Preferably the diglycerol composition comprises at least 80.0 wt. % of diglycerol, preferably at least 85.0 wt. %, more preferably at least 87.0 wt. %, most preferably at least 90.0 wt. %.

The present invention also relates to a partial ester of a carboxylic acid and a polyhydric alcohol, wherein as the polyhydric alcohol use is made of a diglycerol composition which comprises at least 75 wt. % of diglycerol, preferably at least 80.0 wt. % of diglycerol, preferably at least 85.0 wt. %, more preferably at least 87.0 wt. %, most preferably at least 90.0 wt. % and wherein as the carboxylic acid use is made of a fatty acid composition which contains at least one C8-C22 fatty acid.

Optimum lubrication properties and reduction of wearing may be achieved when in the ester use is made of a diglycerol composition which contains at least 90.0 wt. % of non-cyclic diglycerol isomers, preferably at least 95.0 wt. %, more preferably at least 97.5 wt. %, most preferably at least 99.0 wt. %. By ensuring that the concentration of cyclic isomers of diglycerol in the diglycerol composition is as small as possible, esters are provided with good lubricating film forming properties, at minimum risk that the carboxylic acid esters of cyclic diglycerol isomers would adversely affect the homogeneity of the lubricating film.

In order to permit achieving optimum lubrication properties, maximise friction reduction properties and provide a lubricating film with optimum affinity for the surface to be lubrified, the sum of triglycerol, tetraglycerol and higher glycerols in the diglycerol composition will usually be less than 20.0 wt. %, preferably less than 15.0 wt. %, more preferably less than 13.0 wt. %, most preferably less than 10.0 wt. %, even more preferably less than 2.5 wt. %.

Polyol.

The polyhydric alcohol used to produce the partial ester of the present invention will usually comprise a diglycerol composition, and often it will consist of a diglycerol composition. Within the scope of the present invention "diglycerol composition" encompasses a composition which mainly comprises diglycerol $C_6H_{14}O_5$ as a compound, but which besides diglycerol as a compound may contain other polyol compounds such as for example monoglycerol and triglycerol, although some tetraglycerol, pentaglycerol, hexaglycerol and possibly higher polyols, may be present as well. It appears that commercially available diglycerol is usually a mixture of the afore-mentioned components.

The polyhydric alcohol used according to the present invention preferably contains at least 75.0 wt. % of diglycerol $C_6H_{14}O_5$, preferably at least 80.0 wt. %, more preferably at least 85.0 wt. %, most preferably at least 87.0 wt. %, sometimes even more than 90.0 wt. %. For specific applications the use of a polyhydric alcohol may be envisaged which contains at least 92.5 wt. %, preferably at least 95.0 wt. % of diglycerol as a compound.

The concentration of monoglycerol in the diglycerol composition is preferably smaller than 2.5 wt. %, preferably it will be smaller than 2.0 wt. %, more preferably smaller than 1.0 wt. %, most preferably smaller than 0.5 wt. %.

Triglycerol may be present in the diglycerol composition, and if present its concentration will usually be smaller than 25.0 wt. %, preferably smaller than 20.0 wt. %, more preferably smaller than 15.0 wt. %, often below 10.0 wt. % or even below 7.5 wt. %. Tetraglycerol may be present as well, and if present its concentration will usually be smaller than 5.0 wt. %, preferably smaller than 2.0 wt. %, more preferably be smaller than 1.0 wt. %, often below 0.5 wt. %. Where present, the concentrations of penta- and hexaglycerol will usually be low, mostly smaller than 2.5 wt. %, preferably smaller than 1.0 wt. %, often smaller than 0.5 wt. %. Preferably however, the sum of triglycerol, tetraglycerol and higher glycerols in the diglycerol composition is less than 20.0 wt. %, preferably less than 10.0 wt. %, more preferably less than 5.0 wt. %, sometimes smaller than 2.5 wt. %. The concentration of higher glycerols in the diglycerol composition is preferably kept within the limits described above, as the presence of such higher polyols may result in an ester with reduced affinity for the surface that needs lubrication and reduced lubricating properties, leading to a higher risk to wearing of the fuel or engine oil contact surface, as well as an increased friction between moving parts.

Within the scope of the present invention "diglycerol" refers to diglycerol $C_6H_{14}O_5$ as a compound, which includes the usual isomers of diglycerol. Within the scope of the present invention "diglycerol" includes the non-cyclic or acyclic isomers of diglycerol including α,α'-diglycerol, α,β-diglycerol, β,β'-diglycerol represented by the formulae below, as well as cyclic isomers of diglycerol:

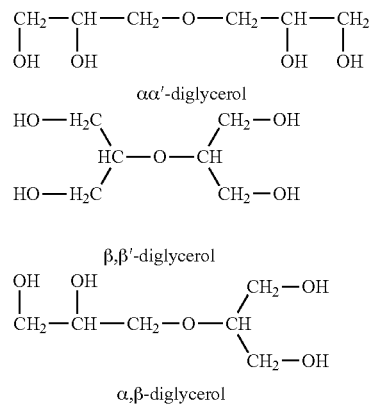

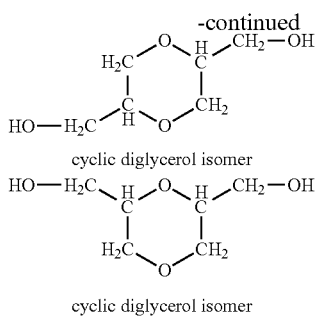

cyclic diglycerol isomer cyclic diglycerol isomer

In the diglycerol composition used to produce the partial esters of the present invention, diglycerol may be a mixture comprising the above mentioned isomers in widely varying concentrations. Preferably however α,α'-diglycerol will be present as the main component; β,β'-diglycerol, α,β-diglycerol and the cyclic isomers will usually be present as minor components. The concentration of cyclic diglycerol isomers will usually not be more than 10.0 wt. %, preferably less than 7.5 wt. %, more preferably less than 5.0 wt. %, most preferably less than 2.5 wt. %. It is preferred that the concentration of acyclic isomers of diglycerol is as high as possible as this permits to provide a lubricant with good with good film forming properties and to build a lubricating film on the surface to be lubrified with the best possible homogeneity. The inventors have observed that the higher the content of acyclic diglycerol isomers, the more uniform the physical properties and physical behaviour of the lubricating composition will be, with improved lubrication and friction reduction properties and in reduced wearing as a result. The concentration of cyclic isomers of diglycerol is preferably kept to a minimum, as they tend to adversely affect the homogeneity of the lubricant film, thus increasing wearing and friction.

Examples of commercially available diglycerol composition include those available from Solvay (Belgium) with a relatively high purity, which often contain at least 90.0 wt. % of diglycerol, the remainder being mainly glycerol and triglycerol, although some tetraglycerol, pentaglycerol and hexaglycerol may be present as well.

Fatty Acids.

Within the scope of the present invention the partial ester of a carboxylic acid and a polyhydric alcohol comprise a carboxylic acid which is preferably a $C_8$-$C_{22}$, more preferably a $C_{12}$-$C_{22}$ monocarboxylic acid. The monocarboxylic acid may be a linear or branched chain carboxylic acid, it may be saturated or unsaturated and it may be substituted. If so desired, a mixture of two or more carboxylic acids may be used as well. The monocarboxylic acid is preferably a $C_8$-$C_{22}$, more preferably a $C_{12}$-$C_{22}$ fatty acid.

The use of an unsaturated fatty acid or a mixture of two or more unsaturated fatty acids, possibly also containing some saturated fatty acids, may be preferred, as those mixtures are readily commercially available, they often originate from natural renewable sources. Particularly useful unsaturated fatty acids comprise mixtures which comprise oleic acid or ricinoleic acid as the main component. However, mixtures of these fatty acids may also be used.

The carboxylic acid component will usually be of vegetal origin, but animal fats may be suitably used as well. Suitable sources for the carboxylic acid component include fatty acids which originate from vegetal oils for example soybean oil, rape seed oil, sunflower oil, palm oil, tallow oil, olive oil, pecan oil, peanut oil, olive oil, palm kernel oil and coconut oil, fractions of these fats and oils as well as mixtures of two or more of the afore-mentioned fats and oils and fractions thereof. It should be clear that this list of suitable sources for fatty acids is not exhaustive and that other sources may be used as well. Fatty acids which originate from a natural source will usually be commercially available as a mixture of several fatty acids.

According to a first preferred embodiment, mixtures of fatty acids are preferred which have a high content of C18:1, as they provide lubricating agents with extremely good cold stability. These mixtures will be referred to as "oleic acid mixtures". Particularly preferred are those oleic acid mixtures which contain at least 50.0 wt. %, preferably at least 55.0 wt. %, more preferably at least 60.0 wt. %, most preferably at least 65.0 wt. % of C18:1 fatty acid, in particular oleic acid. Within the scope of the present invention, high purity oleic acid compositions which contain at least 90.0 wt. % or at least 95.0 wt. % of C18:1 fatty acid may be used as well. Oleic acid is a mono-unsaturated omega-9 fatty acid found in various animal and vegetable sources, which responds to chemical formula $CH_3(CH_2)_7CH=CH(CH_2)_7COOH$. The preferred oleic acid mixtures will usually contain maximum 25.0 wt. %, preferably maximum 20.0 wt. % of C18:2 fatty acid, to ensure sufficient oxidation stability, and maximum 10.0 wt. %, preferably maximum 7.5 wt. % of C18:3. In high purity oleic acid compositions, the concentration of C18:2 and C18:3 fatty acid will usually be significantly lower. Commercially available oleic acid mixtures will usually contain less than 7.5 wt. %, preferably less than 5.0 wt. % of C18:0 saturated fatty acid; maximum 10.0 wt. %, preferably maximum 7.5 wt. % of C16:0 saturated fatty acid; maximum 7.5 wt. % preferably maximum 5.0 wt. % of saturated and unsaturated fatty acids containing more than 18 carbon atoms and maximum 7.5 wt. % preferably maximum 5.0 wt. % of saturated and unsaturated fatty acids containing less than 16 carbon atoms. In high purity oleic acid compositions, the concentration of the aforementioned compounds will usually be significantly lower. The invention thus provides lubricating agents with sufficient oxidation stability, which are capable of forming a lubricating film with the highest possible homogeneity, with optimised lubrication properties as well as optimised cold stability. Oleic acid mixtures having the above described composition may be obtained by more or less extensive fractionation of the fatty acid sources.

According to a second preferred embodiment, mixtures of fatty acids are preferred which have a high content of substituted C18:1 fatty acids, in particular C18:1 fatty acids substituted with a hydroxyl group such as ricinoleic acid. Particularly preferred are those ricinoleic acid mixtures which contain at least 60.0 wt. %, preferably at least 65.0 wt. %, more preferably at least 70.0 wt. %, most preferably at least 75.0 wt. % of ricinoleic acid, and these will hereafter be referred to as "ricinoleic acid mixture". Ricinoleic acid is a mono-unsaturated omega-9 fatty acid, which responds to chemical formula $CH_3(CH_2)_5(CHOH)(CH_2)CH=CH(CH_2)_7COOH$. Preferred ricinoleic acid mixtures will usually contain maximum 15.0 wt. %, preferably maximum 10.0 wt. % of C18:2 linoleic fatty acid, maximum 10.0 wt. %, preferably maximum 7.5 wt. % of 018:1 oleic fatty acid maximum 5.0 wt. %, preferably maximum 2.5 wt. % of C18:0 stearic acid to ensure good cold stability and sufficient oxidation stability. Ricinoleic acid mixtures having the above described composition will usually be obtained by more or less extensive fractionation of the corresponding fatty acid sources.

According to a third preferred embodiment, other preferred fatty acid mixtures are those containing saturated carboxylic acids, in particular lauric acid C12:0. Main sources of lauric acid or dodecanoic acid include coconut oil and palm kernel oil. Preferred lauric acid mixtures are those which contain at least 90.0 wt. % of lauric acid, preferably at least 95.0 wt. %, more preferably at least 98.0 wt. %, most preferably at least 99.0 wt. %. Impurities present in the lauric acid will usually include some C14 myristic acid and some C10:0 fatty acid.

In order to achieve optimum film forming properties and a film which is as homogeneous as possible in relation to composition and physical properties, preferably a fatty acid composition is used in which one of the fatty acids is present as a major component, preferably in a concentration of at least 50.0 wt. %, preferably at least 60.0 wt. % or 65.0 wt. %, more preferably at least 70.0 wt. % or 75.0 wt. %, most preferably at least 90.0 wt. % or 95.0 wt. %.

Esterification Reaction.

The partial esters of a diglycerol composition according to the present invention may be produced by partial esterification of the diglycerol composition in the presence of the carboxylic acid or carboxylic acid mixture. Esterification will usually be carried in the well known, conventional reaction conditions, according to which the carboxylic acid, in particular the fatty acid is supplied in stoichiometric excess with respect to the diglycerol, to achieve the envisaged degree of esterification of the polyol. The degree of esterification is not critical to the invention and may vary within some ranges. The esterification may be carried out at a temperature of between 150 and 230° C., the temperature may vary in the course of the reaction. Within the scope of the present invention, the ratio fatty acid:diglycerol is preferably selected so as to achieve a density of fatty acid residues attached to the diglycerol, which ensures optimum lubrication and wearing reduction. As will be evidenced below, the optimum ratio may vary with the nature of the diglycerol composition and/or the nature of the fatty acid or fatty acid mixture.

Where a lauric fatty acid mixture is used to produce the partial ester of diglycerol, reaction conditions will usually be adapted such that a minimal degree of esterification of at least 0.90 is obtained, preferably at least 1.0. Where an oleic acid or ricinoleic fatty acid mixture is used to produce the partial ester of diglycerol, reaction conditions will usually be adapted such that a minimal degree of esterification of at least 0.75 is obtained, preferably at least 0.80, more preferably at least 0.90, most preferably more than 1.0. With degree of esterification is meant the ratio diglycerol mono-ester to diglycerol di-ester With the esterification degree in the afore mentioned preferred ranges, a good miscibility of the lubricity improver of this invention is observed with the usual fuel and lubricating compositions, at minimum risk to settling of the lubricity improver and phase separation from the fuel or lubricating composition. Esters having an esterification degree within the afore mentioned ranges and preferred ranges have been found to be capable of showing sufficiently strong polar interactions with a metal surface, thereby improving lubrication ability.

Esterification may be carried out enzymatically, for example according to the process described by E. Garcia et al, in the Journal of Surfactants and detergents, 2001, vol. 4, no 3, 257-262. However, conventional alkaline catalysts may be used as well.

Partial esters of diglycerol according to the present invention will usually contain a certain amount of tri- and tetra-esters and higher esters of diglycerol, which may be up to 20 wt. % or 30 wt. % or more. Preferably however, the amount of tri- and tetra-esters and higher esters is as small as possible, as their presence may give rise to increased wearing. For example the amount of tri- and tetra-esters and higher esters is less than 5.0 wt. %, preferably less than 2.5 wt. %, more preferably less than 1.0 wt. %.

Partial esters of ricinoleic and oleic acid will usually be intended for applications where a good cold stability at temperatures below 10° C. or even below 0° C. are envisaged. Partial esters of lauric acid will usually be intended for applications where good oxidation stability is envisaged.

The scope of the present invention also encompasses the use of mixed esters of lauric acid and oleic acid with diglycerol, and the use of mixtures of diglycerol esters of oleic acid and diglycerol esters of lauric acid.

Use.

The compositions of the present invention are suitable for use in a wide variety of applications where lubrication is at stake. For example the compositions of the present invention may be used as an additive for fuel compositions such as for example the common petroleum distillates, for example diesel oil, fuel for turbines etc. These fuel compositions mainly consist of hydrocarbons and their distillation temperature at atmospheric pressure is between about 130 and 400° C. The compositions of the present invention may however also be used to further improve or alter the lubrication properties of lubrication compositions, such as lubricating oils, for example engine oils.

The compositions of the present invention may mainly consist of a partial ester of a C8-C22 fatty acid and a diglycerol composition. The compositions of the present invention may however also be used as a mixture of fatty acid esters of monoglycerol and a diglycerol composition, or a mixture of fatty acid esters of monoglycerol, a diglycerol composition and higher polyols.

The amount of lubricity improver according to the invention to be incorporated may vary according to the envisaged application. Commonly used industrial standards involve incorporation of about 200-400 ppm of lubricant when used as a fuel additive mainly for the purpose of reducing wearing. When used in lubricating oil compositions mainly for the purpose of reducing friction, the lubricating additive will usually be added in amounts of below 5.0 wt. % often about 0.5 wt. % with respect to the total weight of the lubricating composition.

The invention is further illustrated in the examples and comparative examples below.

In the examples, the pour point and cold stability have been measured according to ASTM D97-04. Lubrication and wearing have been measured according to ASTM standard D6079-04 (HFRR). Although this test permits to determine wearing scars with a sufficient degree of accuracy, measurement of friction coefficients in the order of magnitude of 0.5 and certainly 0.2 cannot be done with sufficient accuracy. Therefore friction coefficients have been determined using a MUST microtribometer from Falex as follows.

The measuring element of this device is a 25 by 50 mm cantilever with a given tangential ($k_t$) and normal stiffness ($k_n$). The cantilever deflections in X and Z directions are independent from each other, and are detected with a set of optical sensors (FOS) placed in normal and tangential direction of the cantilever. The tip of a FOS sensor contains a bundle of glass fibers, which consist of both transmitters and receivers of light. Two mirrors attached to the cantilever have reflecting surfaces towards −X and +Z directions. The two tangential and normal sensors are placed approximately 1 mm away from the mirrors. The light radiated from the light transmitters is received back by the bundle of receptors after reflection from the mirror on the cantilever. These received signals are converted to electrical signals by opto-electronic transducers. The sensing characteristic of the optical fiber, $U_y=f(y)$, with, y, being the distance from the mirror, is determined by the photometric distance law. On deflection of the cantilever either in tangential or normal direction, the intensities of the received light change leading to subsequent changes in the voltage. These differential voltages are converted to forces using the FOS calibration files already recorded in the instrument. The counterbody is glued at one end of this cantilever and the sample to be tested is placed on a reciprocating table. The relative position of the counterbody versus the sample can be altered with the help of fully automated positioning controls. By calculating the deflections in tangential direction dx, the friction force between the material couple is measured. Depending on the range of normal forces required, cantilevers with different stiffness are used. For instance, a steel cantilever with low normal stiffness 50 N/m and tangential stiffness 100 N/m is used for normal forces in the range of 50 µN to 1 mN, while a steel cantilever with normal stiffness 520 N/m and tangential stiffness 1025 N/m is used in the range of 10 to 250 mN. By using cantilevers with different stiffness values, the normal force can be varied from mN down to µN. Two test configurations unidirectional test or ball-on-disk and bi-directional reciprocating sliding tests were performed with this test principle. In ball-on-disk tests, a ball comes in contact with oil containing disk and presses it with certain force. On reaching required contact force, the disk starts rotating. Due to friction the cantilever deflects and the friction force is measured. In bi-directional sliding or reciprocating tests, the counterbody ball presses against oiled disk and the moves in a linear reciprocating manner. Thus one forward-backward movement of the table refers to one cycle. Bi-directional or reciprocating sliding is commonly noticed in the cylinder-piston assembly of an engine. The major difference between the two methods is only the way two surfaces move relative to each other.

A standard automotive 52100 steel disk with dimensions of Ø24=7.9 mm, hardness 60 Rc was used in these tests. The surface of the disks was lapped with peak-to-valley roughness Rz between 0.5 µm-0.65 µm. A chrome steel ball 3.175 mm in diameter was used as the counterbody. The reason for selecting 100Cr6 ball is because piston rings are commonly chrome plated. For the tests, 2 ml oil was applied and evenly distributed on the surface by using a disposable pipette.

COMPARATIVE EXAMPLE I-VI AND EXAMPLE 1

Influence of the Degree of Polymerisation of Diglycerol on Oleic Acid Ester Friction Reduction Properties Several esters of oleic acid were produced by subjecting an oleic acid composition to an esterification reaction with diglycerol compositions of varying degree of polymerisation as summarised in table 2. The diglycerol contained in the diglycerol composition contained about 75 wt. % of $\alpha,\alpha'$ diglycerol, 25 wt % of $\alpha,\beta$-diglycerol, the diglycerol composition contained about 7 wt. % of cyclic compounds. The oleic acid composition is commercially available from Oleon and has the composition given below in table 1.

The esterification reaction was carried out as follows. The diglycerol composition and the fatty acid were fed to a stirred 4-way reactor with a volume of 1 liter in the ratio's given in table 2 below. An alkaline catalyst was supplied. Nitrogen gas is supplied to the reactor. As soon as the acid number of the reaction mixture sunk below 1 mg KOH/g, the reaction mixture was neutralised and cooled. The product was filtered. The amount of polyol supplied to the reaction mixture was chosen such that the OH number after the esterification reaction was about 300.

Wearing of a metal part was determined by mixing 200 ppm of the ester of table 2 below with diesel fuel, at 60° C., 50 Hz, loading of 200 g and 1 mm stroke, using HFRR tests according to ASTM method D6079-04 described above.

TABLE 1

| fatty acid composition of oleic acid. | |
|---|---|
| Fatty acid | Weight % |
| C14 | ≤4 |
| C16 | ≤6 |
| C18:0 | ≤2.5 |
| C18:1 | ≥70 |
| C18:2 | ≤18 |
| C18:3 | ≤1 |

TABLE 2

| | Ester | Reactor loading* | Composition of "diglycerol composition" | Wearing (µm) | OH number (mgKOH/g) |
|---|---|---|---|---|---|
| Comparative example I | Glycerol mono-oleate | 1/0.74 | >99.7 glycerol | 330 | 222 |
| Example 1 | Diglycerol mono-oleate | 1/1.13 | 90.7% diglycerol | 251.5 | 336 |
| Comparative example II | Triglycerol mono-oleate | 1/1.41 | 27.9% diglycerol<br>46% triglycerol<br>17.9% tetraglycerol<br>5.6% pentaglycerol<br>2.6% C6 glycerol and higher | 330 | 268 |
| Comparative example III | Tetraglycerol mono-oleate | 1/1.97 | 2% diglycerol<br>40.2% triglycerol<br>35.3% tetraglycerol<br>19.8% penta- and hexaglycerol<br>7.8% heptaglycerol and higher | 389.5 | 290 |
| Comparative example IV | Polyglycerol mono-oleate | 1/1.98 | 3.7% glycerol<br>28.3% diglycerol<br>18.4% triglycerol | 323.5 | 294 |

TABLE 2-continued

| | Ester | Reactor loading* | Composition of "diglycerol composition" | Wearing (μm) | OH number (mgKOH/g) |
|---|---|---|---|---|---|
| Comparative example V | Polyglycerol mono oleate | 1/1.19 | 14.9% Tetraglycerol 12.6% pentaglycerol 13.5% hexaglycerol 8.5% higher than hexaglycerol 56.68% glycerol 28.13% diglycerol 9.13% triglycerol 2.96% tetraglycerol 0.85% pentaglycerol 0.24% hexaglycerol 1.61% higher than hexaglycerol | 313.5 | 280 |
| Comparative example VI | Polyglycerol mono-oleate | 1/1.41 | 3.56% glycerol 59.33% diglycerol 22.65% triglycerol 9.23% tetraglycerol 3.52% pentaglycerol 1.29% hexaglycerol 2.97% higher than hexaglycerol | 328 | 270 |

Reactor loading*= number of moles of alcohol caused to react with number of moles of fatty acid

EXAMPLE 2

Influence of the Degree of the Concentration of Diglycerol in the Diglycerol Composition on Diglycerol Oleic Acid Ester Wearing Reduction Properties Mono-esters of oleic acid were produced by subjecting 1.38 moles of the oleic acid composition of table 1 to an esterification reaction with 1 mole of a diycerol compositions containing 82.0 wt. % of diglycerol as a compound, as summarised in table 3. The esterification reaction was carried out as described in example 1.

TABLE 3

| Concentration of diglycerol in diglycerol composition (wt. %) | Reactor loading (moles alcohol/moles fatty acid) | Wearing (μm) |
|---|---|---|
| Ex. 2 | 82.0 wt. % | 1/1.38 | 334.5 |

EXAMPLE 3a AND 3b

Influence of the Degree of the Concentration of Diglycerol in the Diglycerol Composition on Diglycerol Lauric Acid Ester Wearing Reduction Properties Mono-esters of lauric acid were produced by subjecting a lauric acid composition in the amounts given in table 4 below to an esterification reaction with the amount of diglycerol composition indicated in table 4 below. The diglycerol compositions contained varying amounts of diglycerol as a compound, as summarised in table 4a. The lauric acid composition is commercially available from Oleon and has the composition given in table 4b. The esterification reaction was carried out as described above in example 1.

TABLE 4a

| | Concentration of diglycerol in diglycerol composition (wt. %). | Reactor loading (moles alcohol/moles fatty acid) | Wearing (μm) |
|---|---|---|---|
| Ex. 3a | 72.2 wt. % | 1/0.785 | 436.0 |
| Ex. 3b | 82.0 wt. % | 1/0.782 | 345.5 |

TABLE 4b

| fatty acid composition of lauric acid | |
|---|---|
| Fatty acid | Weight % |
| C14 | |
| C10 | |
| C12:0 | ≥98 |

From table 4a it appears that with increasing purity of the diglycerol wearing may be reduced.

COMPARATIVE EXAMPLE VII-X AND EXAMPLE 4

Influence of the Degree of Polymerisation of Glycerol on Wearing Reduction Properties of Glycerolesters of Lauric Acid Several esters of lauric acid were produced by subjecting a lauric acid composition commercially available from Oleon to an esterification reaction with glycerol compositions of varying degree of polymerisation as summarised in table 5. The esterification reaction was carried out as described above, by supplying fatty acid and diglycerol in a ratio which permitted to achieve the OH number indicated in table 5.

Wearing of a metal part was determined by mixing 200 ppm of the ester of table 2 below with diesel fuel, at 60° C., 50 Hz, loading of 200 g and 1 mm stroke, using HFRR tests according to ASTM method D6079-04 described above.

TABLE 5

| | Ester | Reactor loading (moles alcohol/ moles fatty acid) | Composition of diglycerol | Wearing (μm)† | OH number (mg KOH/g of ester) |
|---|---|---|---|---|---|
| Comparative example VII | Glycerol Mono-laurate | 1/0.95 | >99.7% glycerol | 405.5 | 414 |
| Example 4 | Diglycerol mono-laurate | 1/1.01 | 90.7% diglycerol | 293.5 | 437 |
| Comparative example VIII | Triglycerol mono-laurate | 1/0.80 | 27.9% diglycerol 46% triglycerol 17.9% tetraglycerol 5.6% pentaglycerol 2.6% hexaglycerol and higher | 395.5 | 482 |
| Comparative example IX | Tetraglycerol mono-laurate | 1/0.94 | 2% diglycerol 40.2% triglycerol 35.3% tetraglycerol 19.8% penta and hexaglycerol 7.8% heptaglycerol and higher | 618 | 596 |
| Comparative example X | Polyglycerol mono-laurate | 1/0.78 | 27.6% glycerol 29.8% diglycerol 19.3% triglycerol 11.1% tetraglycerol 6.1% pentaglycerol 3.6% hexaglycerol 2.1% higher than hexaglycerol | 436 | 568 |

The results of table 5 show that lubrication properties provided by a mono glycerol ester as well as those of tri-, tetra- and polyglycerol esters remain significantly behind when compared to the ester of diglycerol. Wearing was found to be more pronounced with increasing degree of polymerisation of glycerol to tri-, tetra- and polyglycerol.

EXAMPLES 5-11

Influence of the Ratio Mono-Ester of Diglycerol:Di-Ester of Diglycerol on Wearing Reduction Properties for Esters of Oleic Acid Esters of oleic acid and diglycerol with a varying degree of esterification, i.e. a varying ratio of diglycerol mono-oleate with respect to diglycerol di-oleate, were produced using the procedure described above in example 1, by subjecting the oleic acid composition of table 1 to an esterification reaction with a diglycerol composition having the composition described in example 1 above. Wearing reduction properties of the thus obtained esters were determined as described above. The results are summarised in table 6.

Wearing of a metal part and friction coefficient were determined by mixing 200 ppm of the ester of table 6 below with diesel fuel, and using this mixture in ASTM test D6079-04.

TABLE 6

| | Wearing (μm) | Molar ratio diglycerol mono-oleate/diglycerol di-oleate |
|---|---|---|
| Example 5 | 344 | 0.72 |
| Example 6 | 307.5 | 0.81 |
| Example 7 | 300.5 | 1 |
| Example 8 | 289 | 1.14 |

TABLE 6-continued

| | Wearing (μm) | Molar ratio diglycerol mono-oleate/diglycerol di-oleate |
|---|---|---|
| Example 9 | 268 | 1.39 |
| Example 10 | 267 | 1.41 |
| Example 11 | 257 | 1.44 |

EXAMPLES 12-17

Influence of the Ratio Mono-Ester of Diglycerol:Di-Ester of Diglycerol on Wearing Reduction Properties for Esters of Ricinoleic Acid Esters of ricinoleic acid and diglycerol were produced with a varying ratio of diglycerol mono-ricinoleate with respect to diglycerol di-ricinoleate using the procedure described above for example 5-11, as shown in table 7a. Friction reduction properties were determined as described above. The diglycerol composition used to produce the esters had the composition described in example 2. Ricinoleic acid had the composition shown in table 7b below. The results are summarised in table 7a.

From table 7a it appears that for esters of diglycerol and ricinoleic acid optimum wearing reduction is provided with a molar ratio diglycerol mono-ricinoleate/diglycerol di-ricinoleate of about 1.15.

Wearing of a metal part and friction coefficient were determined by mixing 200 ppm of the ester of table 7a below with diesel fuel, using ASTM D6079-04 method.

TABLE 7a

|  | Wearing (μm) | Molar ratio diglycerol mono-ricinoleate/diglycerol di-ricinoleate |
|---|---|---|
| Example 12 | 366 | 0.81 |
| Example 13 | 341 | 0.95 |
| Example 14 | 291.5 | 1.14 |
| Example 15 | 302.5 | 1.24 |
| Example 16 | 368.5 | 1.40 |
| Example 17 | 342 | 1.49 |

TABLE 7b composition of ricinoleic acid.

| Fatty acid | wt. % |
|---|---|
| C16:0 | <5.0 |
| C18:1 | >80.0 |
| C18:1 | <10.0 |
| C18:2 | <15.0 |
| C18:3 | <5.0 |

EXAMPLES 18-25

Influence of the Ratio Mono-Ester of Diglycerol:Di-Ester of Diglycerol on Wearing Reduction Properties for Esters of Lauric Acid Esters of lauric acid and diglycerol with a varying degree of esterification, i.e. ratio diglycerol mono laurate with respect to diglycerol dilaurate, were produced as described above by subjecting lauric acid with the composition given in table 4b to an esterification reaction with the diglycerol composition of example 2.

Wearing reduction properties were determined as described above. Wearing of a metal part was determined by mixing 200 ppm of the ester of table 8 below with diesel fuel, using ASTM D6079-04. The results are summarised in table 8.

From table 8 it appears that for esters of diglycerol and oleic acid optimum wearing reduction properties are provided by partial esters with a molar ratio diglycerol mono laurate/diglycerol dilaurate of more than 1.0.

TABLE 8

|  | Wearing (μm) | Molar ratio diglycerol mono laurate/diglycerol dilaurate |
|---|---|---|
| Example 18 | 379.5 | 0.61 |
| Example 19 | 350 | 0.72 |
| Example 20 | 366.5 | 0.85 |
| Example 21 | 342 | 0.93 |
| Example 22 | 334 | 1.06 |
| Example 23 | 317.5 | 1.14 |
| Example 24 | 306 | 1.31 |
| Example 25 | 359.5 | 1.42 |

COMPARATIVE EXAMPLE XI-XIII AND EXAMPLES 26-27

Influence of the Nature of the Fatty Acid on Friction Reduction Properties of the Diglycerol Ester In comparative example XVI-XVIII use was made of erucid acid for producing the diglycerolmono-erucate ester. Erucic acid had the composition given in table 9:

TABLE 9 fatty acid composition of erucic acid and elaidic acid

| Fatty acid | Wt. % Erucic acid | Elaidic acid |
|---|---|---|
| C12 |  | 1.66 |
| C16 | <1.0 |  |
| C16:0 |  | 7.49 |
| C16:1 |  | 0.12 |
| C17:1 |  | 0.14 |
| C18:0 | <0.5 | 2.82 |
| C18:1 | <1.5 | 82.62 |
| C18:2 | <1.5 | 0.63 |
| C18:3 | <0.5 |  |
| C20:0 | <.6 | 0.30 |
| C20:1 | <4.0 | 0.57 |
| C22:0 | <2.0 |  |
| C22:1 | 90.0-94.0 |  |
| C22:2 | <2.0 |  |
| others | <1.0 | 3.65 |

In example 26 and 27 respectively use was made of an oleic acid composition and a lauric acid composition as described in table 1 and 4b. Wearing of a metal part and friction reduction coefficient were determined by mixing 200 ppm of the ester of table 10 below with diesel fuel, and using ASTM D6079-04. The results are summarised in table 10.

TABLE 10

|  | Product | Wearing (μm) |
|---|---|---|
| Comparative example XI | Diglycerolmono-erucate | 331.5 |
| Comparative example XII | Diglycerol mono-elaïdate | 343 |
|  | Diglycerol mono-ricinoleate | 291.5 |
| Comparative example XIII | Diglycerol mono-linoleate | 322.5 |
| Example 26 | Diglycerol mono-laurate | 293.5 |
| Example 27 | Diglycerol mono-oleate | 251.5 |

TABLE 11 cold stability of several esters of diglycerol and different fatty acids.

|  | Product | Cloud point (° C.) | Pour point (° C.)/Melting Point (° C.) |
|---|---|---|---|
| Comparative example XXI | Glycerol monolaurate | Too hight to be detectable | 42 (melting point) |
| Comparative example XXII | Glycerol monooleate | <10 | 6 |
| Example 26 | Diglycerol monooleate | 12 | −11 (pour point) |
| Example 27 | Diglycerol monolaurate | 26 | 19 (pour point) |

From table 11 it appears that esters of diglycerol have a lower pour point/melting point than their corresponding glycerol esters, which permits their use at a larger temperature interval and at low temperature

EXAMPLE 28

Evaluation of Friction Coefficient of a Diesel Oil Composition Containing Varying Amounts of the Lubricating Composition of this Invention Use was made of a ball-on-flat test, at a loading of respectively 50 mN (240 MPa contact pressure) and 150 mN (320

MPa contact pressure) load, and a speed of 0.5 and 2.5 mm/s, 50 reciprocating cycles. The results are shown in FIG. 1.

Figure 1:
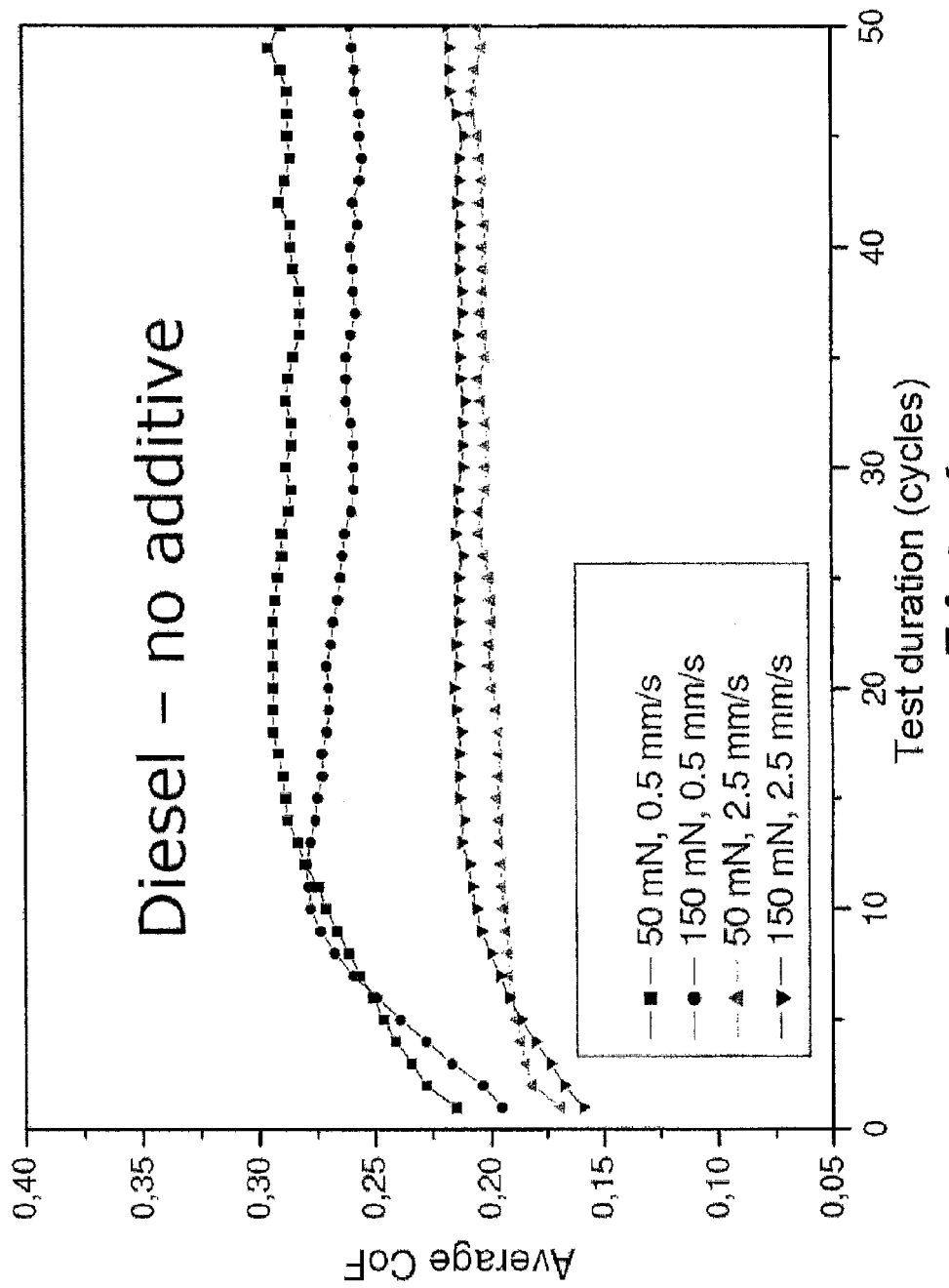
FIG. 1 shows the average friction coefficient when using diesel as a fuel composition with no addition of a friction reducing compound for different loadings and speeds.
Figure 2:
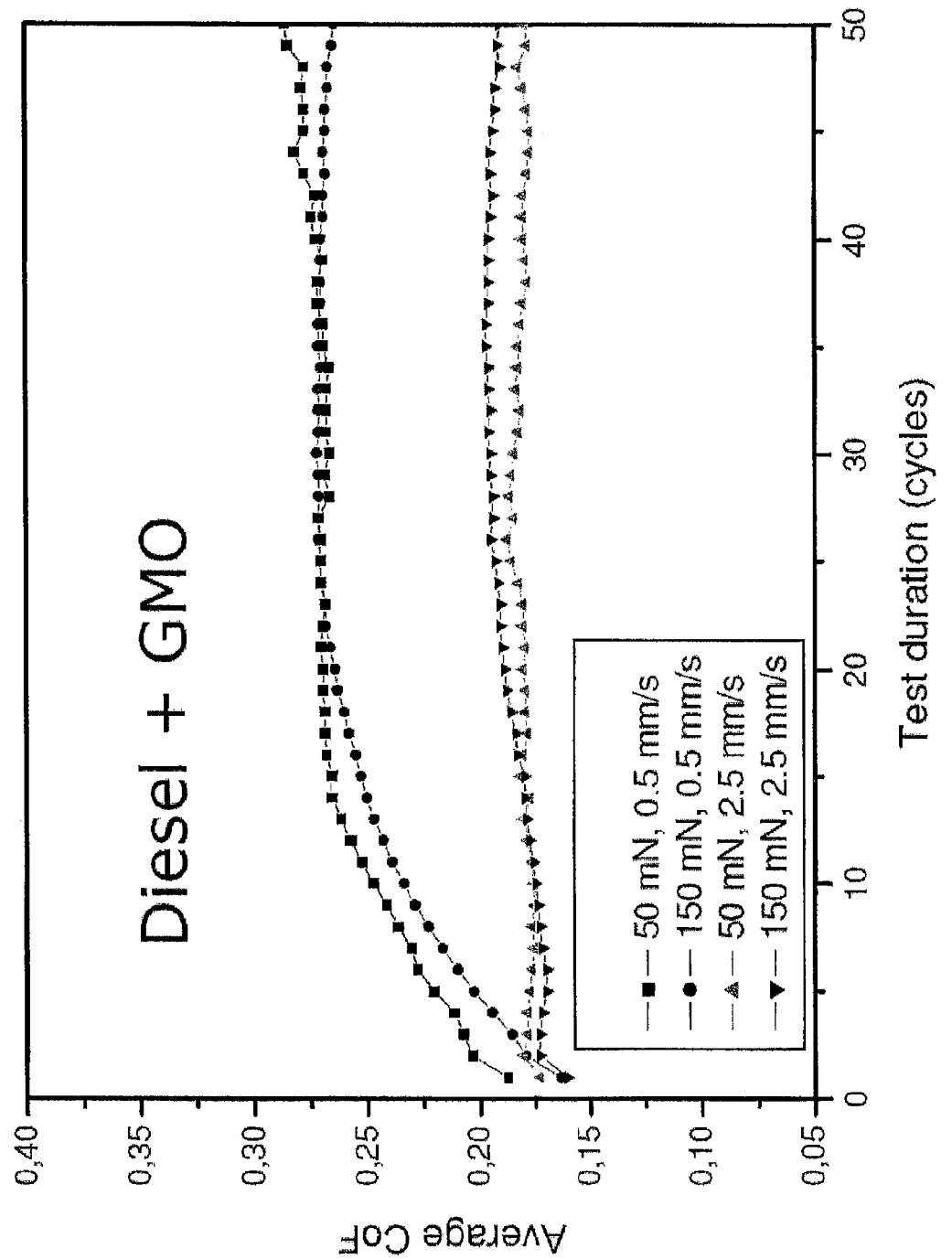
FIG. 2 shows the friction coefficient of a diesel composition to which glycerol mono-oleate had been added as a friction reducing compound for different loadings and speeds.
Figure 3:
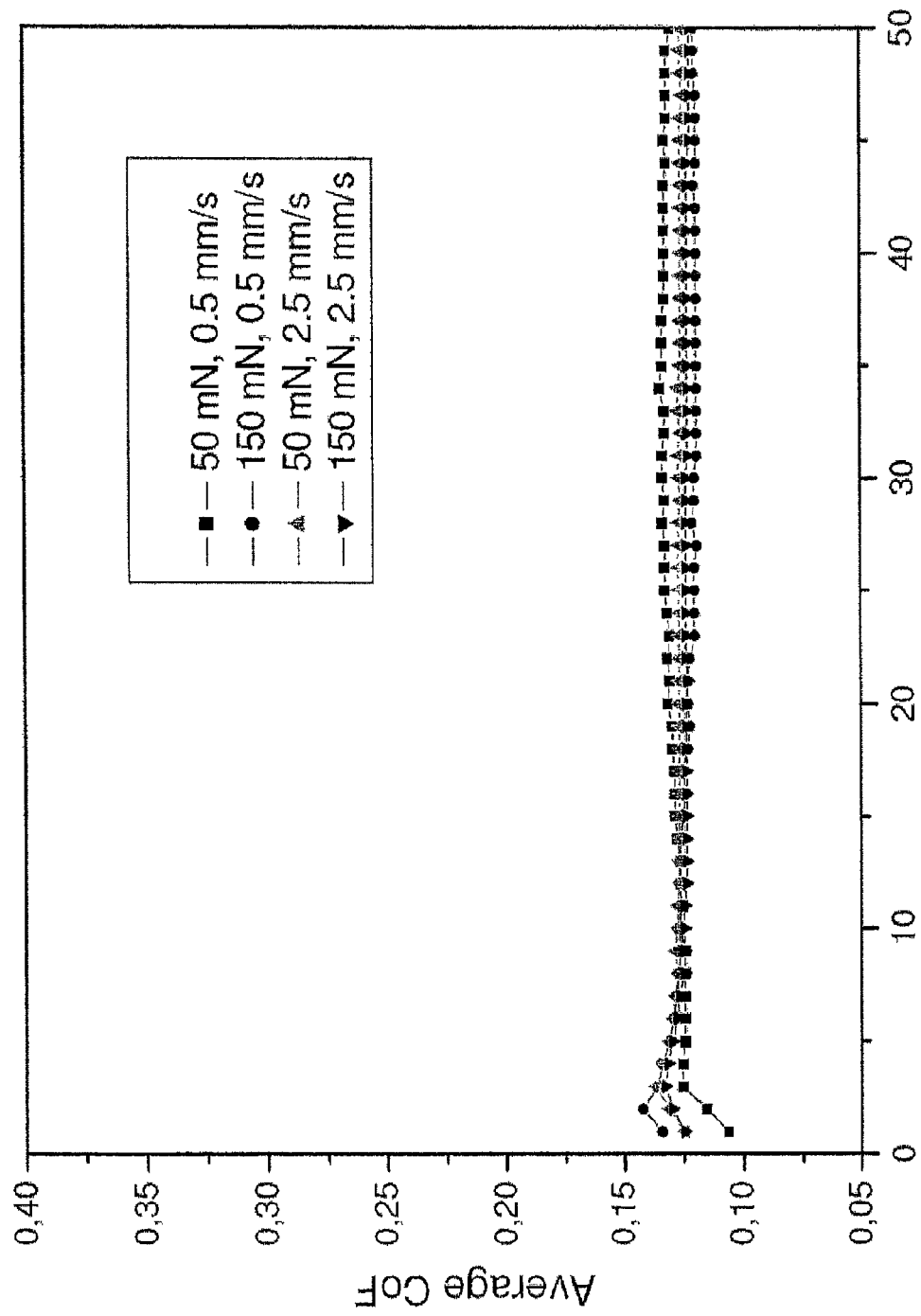
FIG. 3 shows the friction coefficient of a diesel composition to which an ester of diglycerol and oleic acid according to the invention had been added.

From the comparison of the results shown in FIG. 3 with FIGS. 2 and 1 it becomes clear that upon addition of the ester of the present invention the friction coefficient may be significantly reduced and that the friction coefficient varies within small ranges only upon varying loading and velocity.

Figure 4:
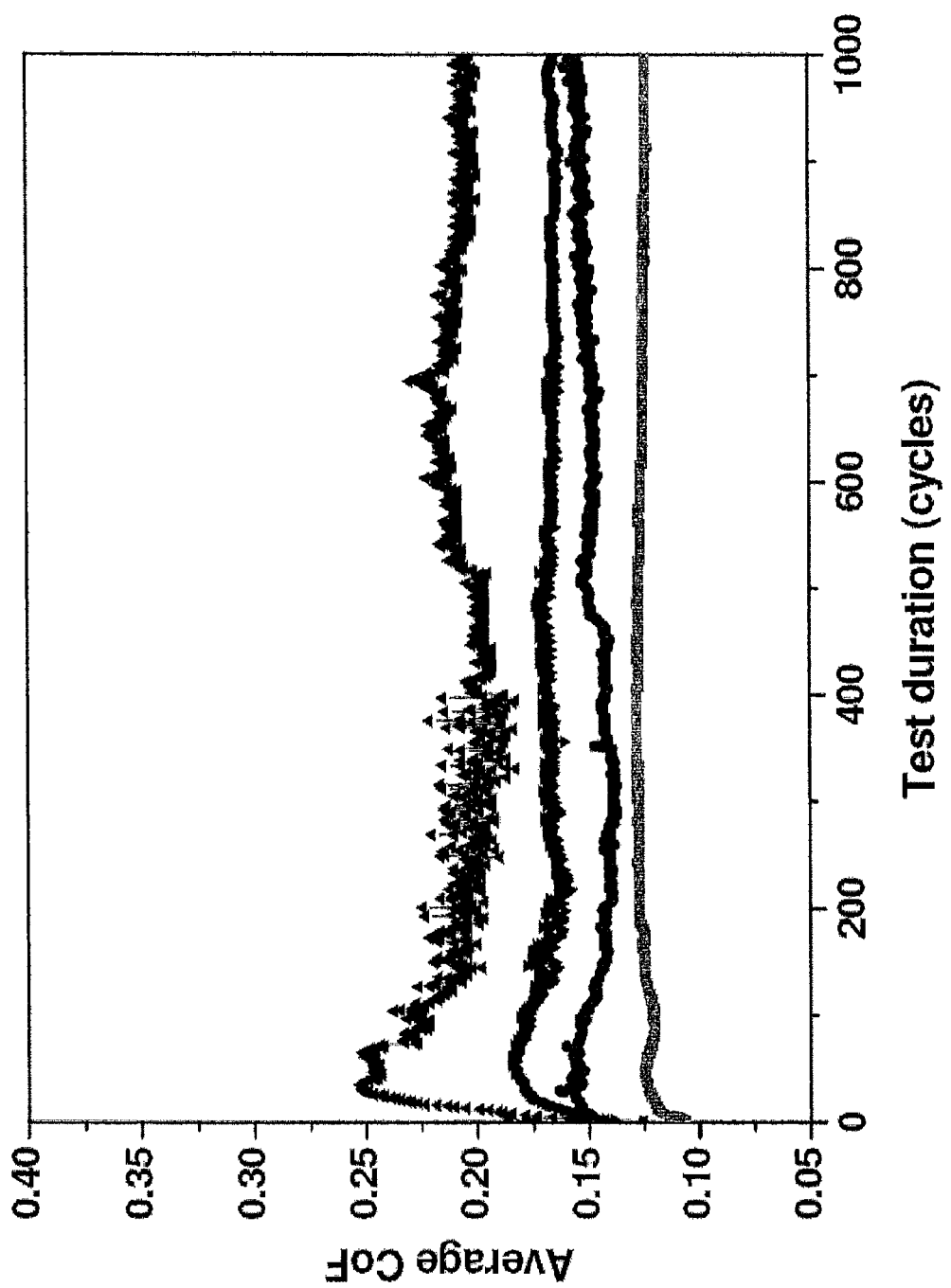

FIG. 4 shows the friction coefficient in a duration test with a significantly higher number of cycles, in particular a test at 150 mN, 1000 cycles, 2.5 mm/s. From FIG. 4 it can be seen that even for long periods of use, addition of the ester of the present invention (bottom curve) permits to obtain a reduced friction coefficient when compared to diesel alone (▲), diesel to which glycerol mono-oleate has been added (second curve from bottom ★) and diesel to which a commercially available lubricity improver has been added (second curve from top ▼). This supports the assumption that the reduced wearing achieved by adding the ester of this invention to engine oil or fuel, results therein that the risk to the formation of abrasive particles is reduced, so that long term lubricating properties may be maintained.

It is assumed that the observations described above may be attributed to the ability of the esters of the present invention to form a stable film on the surface to be lubricated, wherein the esters provide a lubricating film with a high affinity and improved adhesion to the surface to be lubricated. The affinity and adhesion have been found to be such that friction may be reduced even after long periods of use.

The invention claimed is:

1. A method of improving the lubricity of a composition comprising adding to said composition a partial ester of a carboxylic acid and a polyhydric alcohol, said polyhydric alcohol being comprised of a diglycerol composition which comprises at least 75.0 wt. % of diglycerol and said carboxylic acid being comprised of a fatty acid composition which contains at least one C8-C22 fatty acid and said diglycerol composition being comprised of α, α' diglycerol as the main component; and wherein the partial ester is comprised of diglycerol mono-ester and diglycerol di-ester and the ratio of diglycerol mono-ester to diglycerol di-ester is at least 0.75.

2. The method according to claim 1, wherein the diglycerol composition comprises at least 80 wt. % of diglycerol.

3. The method according to claim 1, wherein the diglycerol contains at least 90.0 wt. % of non-cyclic diglycerol isomers.

4. The method according to claim 1 wherein the diglycerol composition is comprised of triglycerol, tetraglycerol and higher glycerols, and wherein the sum of triglycerol, tetraglycerol and higher glycerols in the diglycerol composition is less than 20.0 wt. %.

5. The method according to claim 1, wherein the diglycerol contains less than 10.0 wt. % of cyclic isomers of diglycerol.

6. The method according to claim 1, wherein the carboxylic acid contains at least 50.0 wt. % of oleic acid C18:1.

7. The method according to claim 6, wherein the carboxylic acid contains maximum 5.0 wt. % of C18:0, maximum 25.0 wt. % of C18:2, maximum 10.0 wt. % of C18:3 and maximum 5.0 wt. % of fatty acids containing more than 18 carbon atoms.

8. The method according to claim 1, wherein the carboxylic acid contains at least 60.0 wt. % ricinoleic acid.

9. The method according to claim 8, wherein the carboxylic acid contains maximum 15.0 wt. % of C18:2 fatty acid, maximum 10.0 wt. % of C18:1 fatty acid, and maximum 5.0 wt. of C18:0 fatty.

10. The method according to claim 1, wherein the carboxylic acid contains at least 90.0 wt. % of lauric acid.

11. The method according to claim 1, wherein the composition comprises a partial ester of monoglycerol with at least one C8-C22 fatty acid.

12. A partial ester of a carboxylic acid and a polyhydric alcohol, wherein the polyhydric alcohol is comprised of a diglycerol composition which comprises at least 75 wt. % of diglycerol, wherein the carboxylic acid is comprised of a fatty acid composition which contains at least one C8-C22 fatty acid; and wherein the diglycerol composition comprises α, α' diglycerol as the main component; and wherein said partial ester is comprised of diglycerol mono-ester and diglycerol di-ester and the ratio of diglycerol mono-ester to diglycerol di-ester is at least 0.75.

13. The partial ester of claim 12, wherein the diglycerol contains at least 90.0 wt. % of non-cyclic diglycerol isomers.

14. The partial ester according to claim 12, wherein the diglycerol composition is comprised of triglycerol, tetraglycerol and higher glycerols and sum of triglycerol, tetraglycerol and higher glycerols in the diglycerol composition is less than 20.0 wt. %.

15. The partial ester according to claim 12, wherein the diglycerol contains less than 10.0 wt. % of cyclic isomers of diglycerol.

16. The partial ester according to claim 12, wherein the carboxylic acid contains at least 50.0 wt. % of oleic acid C18:1.

17. The partial ester according to claim 12, wherein the carboxylic acid contains at least 60.0 wt. % of ricinoleic acid.

18. The partial ester according to claim 12 wherein the carboxylic acid contains at least 90.0 wt. % of lauric acid.

19. The partial ester according to claim 12, wherein the diglycerol composition comprises at least 80 wt. % of diglycerol.

20. The partial ester according to claim 16, wherein the carboxylic acid contains maximum 5.0 wt. % of C18:0, maximum 25.0 wt. % of C18:2, maximum 10.0 wt. % of C18:3 and maximum 5.0 wt. % of fatty acids containing more than 18 carbon atoms.

21. The partial ester according to claim 17, wherein the carboxylic acid contains maximum 15.0 wt. % of C18:2 fatty acid, maximum 10.0 wt. % of C18:1 fatty acid, and maximum 5.0 wt. of C18:0 fatty acid.

22. The partial ester according to claim 12 comprising a partial ester of monoglycerol with at least one C8-C22 fatty acid.

* * * * *